(12) United States Patent
Woei et al.

(10) Patent No.: US 12,694,577 B2
(45) Date of Patent: Jul. 28, 2026

(54) INTRAPROCEDURE 2D TO 3D REGISTRATION ADJUSTMENT METHOD AND SYSTEM

(71) Applicant: Broncus Medical Inc., San Jose, CA (US)

(72) Inventors: Ernest Woei, San Jose, CA (US); Kun-Chang Yu, San Jose, CA (US); Matthew McTaggart, Grand Cayman (KY); Abbe Smith, Herriman, UT (US)

(73) Assignee: Broncus Medical Inc., San Jose, CA (US)

( * ) Notice: Subject to any disclaimer, the term of this patent is extended or adjusted under 35 U.S.C. 154(b) by 330 days.

(21) Appl. No.: 18/450,911

(22) Filed: Aug. 16, 2023

(65) Prior Publication Data

US 2024/0070933 A1 Feb. 29, 2024

Related U.S. Application Data

(60) Provisional application No. 63/400,044, filed on Aug. 22, 2022.

(51) Int. Cl.
G06T 11/00 (2026.01)
A61B 6/00 (2024.01)
(Continued)

(52) U.S. Cl.
CPC .............. G06T 11/00 (2013.01); A61B 6/463 (2013.01); A61B 6/487 (2013.01); A61B 6/582 (2013.01);
(Continued)

(58) Field of Classification Search
CPC ... G06T 11/00; G06T 3/60; G06T 7/30; G06T 7/70; G06T 2200/24; G06T 2207/30004;
(Continued)

(56) References Cited

U.S. PATENT DOCUMENTS

| | | |
|---|---|---|
| 7,756,316 B2 | 7/2010 | Odry et al. |
| 7,756,563 B2 | 7/2010 | Higgins et al. |
| | (Continued) | |

FOREIGN PATENT DOCUMENTS

| | | | | |
|---|---|---|---|---|
| CN | 103678837 A | * | 3/2014 | ............. A61B 6/504 |
| CN | 108171784 A | * | 6/2018 | ............. G06T 15/04 |
| WO | 2022035584 A1 | | 2/2022 | |

OTHER PUBLICATIONS

International Search Report dated Nov. 17, 2023 of corresponding application PCT/US2023/072318.
(Continued)

*Primary Examiner* — Said Broome
*Assistant Examiner* — Denis Vasiliy Minko
(74) *Attorney, Agent, or Firm* — Batt IP A Law Corporation; Richard Batt

(57) ABSTRACT

A method for correcting location of a virtual target in a patient during a live procedure comprises segmenting the organ and the real target from an initial pre-procedure image data set; receiving a live procedure image data set of the patient including the organ and the real target and camera tracking information; registering the initial pre-procedure image data set and the live image data set; determining a candidate location of a virtual target for the real target based on the initial registration; generating a first image at a first view angle showing the virtual target and the real target; adjusting the candidate location of the virtual target to match the actual location of the real target in the first image; and computing a corrected location for the virtual target based on the adjusting step. Related systems are disclosed.

23 Claims, 17 Drawing Sheets

(51) Int. Cl.

| | |
|---|---|
| *A61B 6/46* | (2024.01) |
| *A61B 6/58* | (2024.01) |
| *G06T 3/60* | (2024.01) |
| *G06T 7/30* | (2017.01) |
| *G06T 7/70* | (2017.01) |

(52) U.S. Cl.
CPC .................. *G06T 3/60* (2013.01); *G06T 7/30* (2017.01); *G06T 7/70* (2017.01); *A61B 6/4441* (2013.01); *G06T 2200/24* (2013.01); *G06T 2207/30004* (2013.01); *G06T 2210/41* (2013.01)

(58) Field of Classification Search
CPC ..... G06T 2210/41; A61B 6/463; A61B 6/487; A61B 6/582; A61B 6/4441; A61B 6/032
See application file for complete search history.

(56) References Cited

U.S. PATENT DOCUMENTS

| | | | |
|---|---|---|---|
| 7,889,905 | B2 | 2/2011 | Higgins et al. |
| 9,265,468 | B2 | 2/2016 | Rai et al. |
| D765,865 | S | 9/2016 | Keast et al. |
| 9,675,420 | B2 | 6/2017 | Higgins et al. |
| 9,693,748 | B2 | 7/2017 | Rai et al. |
| 9,886,760 | B2 | 2/2018 | Liu et al. |
| D820,452 | S | 6/2018 | Rai et al. |
| 2008/0183073 | A1 | 7/2008 | Higgins et al. |
| 2012/0289825 | A1 | 11/2012 | Rai et al. |
| 2015/0208948 | A1 | 7/2015 | Wei et al. |
| 2016/0317233 | A1 | 11/2016 | Hunter et al. |
| 2017/0296136 | A1 | 10/2017 | Rai et al. |
| 2019/0380792 | A1 | 12/2019 | Poltaretskyi et al. |
| 2020/0160541 | A1 | 5/2020 | Liu et al. |
| 2020/0253959 | A1* | 8/2020 | Van Der Aar ......... G16H 20/10 |
| 2020/0405399 | A1 | 12/2020 | Steinberg et al. |
| 2021/0046870 | A1* | 2/2021 | Maekawa .............. H04N 23/80 |
| 2021/0192759 | A1* | 6/2021 | Lang ..................... A61B 34/10 |

OTHER PUBLICATIONS

Long, L., Dongri, S., Review of Camera Calibration Algorithms, Advances in Computer Communication and Computational Sciences, Conference Proceedings of IC4S 2018, vol. 924, pp. 723-732.

Pinar Muyan-Ozcelik, John D. Owens, Junyi Xia, Sanjiv S. Samant. Fast Deformable Registration on the GPU: a CUDA Implementation of Demons. Proceedings of the 2008 International Conference on Computational Science and Its Applications (ICCSA), IEEE Computer Society Press, Jun. 2008.

Written Opinion of ISA/US dated Nov. 17, 2023 of corresponding application PCT/US2023/072318.

* cited by examiner

200

250
DETERMINING CANDIDATE LOCATION OF VIRTUAL TARGET

260
GENERATING A FIRST IMAGE SHOWING THE VIRTUAL TARGET AND THE REAL TARGET

270
ADJUSTING THE CANDIDATE LOCATION TO MATCH THE ACTUAL LOCATION

280
COMPUTING A CORRECTED LOCATION FOR THE VIRTUAL TARGET

INTRAPROCEDURE 2D TO 3D REGISTRATION ADJUSTMENT METHOD AND SYSTEM

CROSS-REFERENCE TO RELATED APPLICATIONS

This claims priority to provisional application No. 63/400,044, filed Aug. 22, 2022, and entitled "INTRAPRO-CEDURE 2D TO 3D REGISTRATION ADJUSTMENT METHOD AND SYSTEM".

FIELD OF THE INVENTION

The present invention relates to surgical procedures and in particular, to assisting physicians with tracking and guidance during surgical procedures.

BACKGROUND OF THE INVENTION

Minimally invasive surgery is surgery performed with only a small incision or no incision at all and is typically performed with an endoscope, bronchoscope, laparoscope, or like instrument.

In a bronchoscopic procedure, for example, a broncho-scope is inserted through the nose or mouth of the patient, advanced through the trachea and into a desired airway. The surgery may then be performed through the working lumen of the bronchoscope. A light source and camera at the tip of the bronchoscope enables the physician to observe the airway wall in real time. A skilled physician can identify their location along the airway and navigate to the desired location along the airway wall.

It is often desirable, however, to supplement endoscopic visualization with radiological guidance (e.g., by taking real time X-ray images of the region with a fluoroscope). In certain procedures radiologic guidance is necessary.

In a transbronchial needle aspiration (TBNA) procedure, for example, a long flexible catheter comprising a needle at the tip is advanced through the working lumen of the bronchoscope to the planned entry site to the target. The needle is then advanced through the airway wall outside of view of the bronchoscope to aspirate a sample of tissue. It is highly desirable or necessary to have fluoroscopy or an alternative means to view and track the needle once it is outside of view of the bronchoscope.

Route planning, guidance and tracking techniques are available to aid the physician reach the target site. Examples of such techniques are described in the literature. See, e.g., U.S. Pat. No. 9,675,420 to Higgins et al. and U.S. Pat. No. 9,265,468 to Rai et al., each of which is incorporated herein by reference in its entirety. In order to carry out such techniques, the live image data of the organ from the fluoroscope must be registered with that of the pre-acquired 3D image data of the organ. Matching may be performed using image-based feature matching. An example of a fast 2D-3D registration is described in U.S. Pat. No. 9,886,760 to Liu et al, incorporated herein by reference in its entirety.

Notwithstanding the above, registration is susceptible to errors in which the live computed 3D model of the organ does not match that of the pre-acquired data. This error is especially prevalent in registration of relatively non-rigid organs such as the lung. Furthermore, target tissue (e.g., a suspect lesion) identified in the 3D model of the anatomy based on the pre-acquired image data may not align with the actual position of the target tissue during the procedure. Errors may arise for a number of reasons including, for example, (a) the patient position for the pre-acquired image data is different than that of the live image data; (b) the point in the patient's breath cycle for pre-acquired image data is different than that of the live image data; and/or (c) the patient is not able to provide a full breath hold when the pre-acquired image data is taken (e.g., a rigid scope may prevent a full breath hold or leakage in the scope adapter). These errors are undesirable for a number of reasons not the least of which is inaccurately displaying a virtual route leading to the virtual target.

A method and system to cure the above-mentioned errors is therefore desirable.

SUMMARY OF THE INVENTION

A method and system for correcting location of a virtual target in a patient during a live procedure comprises: receiv-ing a pre-procedure image data set (e.g., CT image data set) of the patient including an organ and a real target; segment-ing the organ and the real target from the pre-procedure image data set; receiving a live image data set of the patient (e.g., procedure fluoroscope image data including camera tracking information corresponding to the images); register-ing the pre-recorded image data set and the live image data set; determining a candidate location of a virtual target for the real target based on the initial registration; generating a first image at a first view angle showing the virtual target and the real target; adjusting the candidate location of the virtual target to match the actual location of the real target in the first image; and computing a corrected location for the virtual target based on the adjusting step.

In embodiments, the method further comprises generating a second image at a second view angle showing the virtual target and the real target; adjusting the candidate location of the virtual target to match the actual location of the real target in the second image; and wherein computing the corrected location for the virtual target is based on the adjusting step performed on the first image and the adjusting step performed on the second image.

In another embodiment of the present invention, a system or workstation includes at least one processor operable to receive a pre-procedure image data set of the patient includ-ing an organ and a real target; segment the organ and the real target from the pre-procedure image data set; receive a live image data set of the patient including camera tracking information corresponding to the images; register the pre-recorded image data set and the live image data set; deter-mine a candidate location of a virtual target for the real target based on the initial registration; and compute a corrected location for the virtual target based on receiving an updated or adjusted location of the virtual target.

In embodiments, the processor is further operable to: generate a second image at a second view angle showing the real target and the virtual target; and compute the corrected location for the virtual target based on the user adjustment to the candidate location performed on the first image and user adjustment to the candidate location performed on the second image.

In embodiments, the system or workstation is arranged or in the form of a desktop, portable or laptop computer.

In embodiments, a graphical user interface includes a plurality of windows showing different image views of the real and virtual target, and at least one panel for accepting user input and instructions.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s)

to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there is plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is to be appreciated that unless defined otherwise, all technical and scientific terms used herein have the same meaning as commonly understood by one of ordinary skill in the art to which this invention belongs.

Operating Room and Workstation Overview

Figure 1:
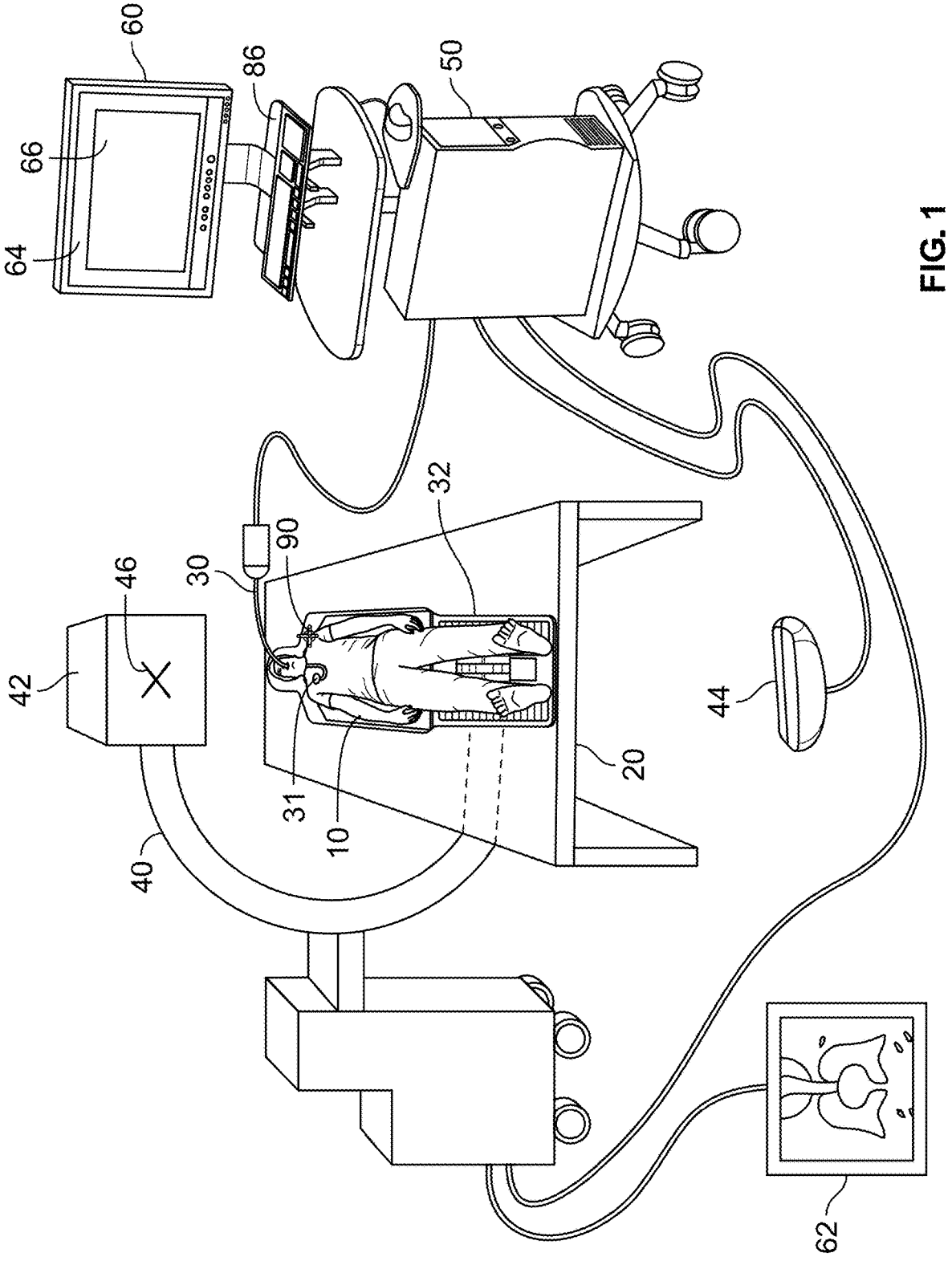
FIG. 1 is a schematic diagram of an operating room environment including a workstation in accordance with an embodiment of the invention.

FIG. 1 illustrates a schematic diagram of a surgical setting in an operating room including a workstation 50 in accordance with the present invention. A subject 10 is shown on a calibrated patient board 32 on an operating table 20 with a surgical device 30 positioned and extending into a lung of the subject. The surgical device 30 has a distal working end or tip 31 which has been passed through the subject's mouth, the trachea, a bronchi, and into the lung. Although the surgical device 30 shown in FIG. 1 is intended to represent an endoscope, namely, a bronchoscope, the invention is not so limited.

The surgical device may be a wide range of devices, instruments, implants, and markers which are visible under fluoroscopy, have a portion which is visible under fluoroscopy, or be modifiable such that it is visible under fluoroscopy. Examples, without limitation, include catheters, sheaths, needles, ablation devices, forceps, brushes, biopsy needles, stents, valves, coils, seeds, and fiducial markers.

A fluoroscope 40 takes real time fluoroscopic video of the subject. Video frames of the video or images are collected or received by workstation 50 for processing. Real time images may also be displayed on a video monitor 62.

The location and pose of the fluoroscopy camera 42 are tracked with a calibrated tracking sensor 44. In the fluoroscopy unit shown in FIG. 1, an optically visible symbol 46 is observed by the optical tracking sensor 44 to provide to workstation 50 information about the location, orientation and pose of the fluoroscopy camera 42 in real time (sometimes referred to herein as "camera tracking information" unless the context clearly indicates otherwise). The optical tracking sensor 44 may be positioned on any fixed surface including the floor, wall, ceiling, or a table. Optionally, the optical tracking sensor 44 may be positioned on a movable platform that can be locked in place. An example of an external sensor is the Polaris Spectra tracker manufactured by NDI in Waterloo, Ontario, Canada. The tracking sensor 44 is configured to detect the location of a tool 46 (and optionally, to detect the tool 90 to track pose of the patient board 32) which may be in the form of a cross-like symbol as shown. Although the tracking sensor shown in this embodiment is optically based, other techniques (for example, electromagnetic) to track the fluoroscopic camera or patient board may be employed and are in accordance with the present invention.

Next, and as discussed in more detail herein, the location of the target tissue shown in the live video from the fluoroscope unit 40 is registered or mapped to the 3D location in a model of the organ arising from a pre-acquired image dataset of the patient (e.g., CT data).

Display 60 is operable with workstation 50 to show a number of types of images including 3D model views, 2D model fluoroscopy views, real fluoroscopy views, real endoscopic views, model endoscopic views, and a wide range of information superimposed on the views such as without limitation planning information, region of interests, virtual target markers, vessels, virtual obstacles, real devices, virtual devices, routes to a target, notes and indicia provided by the user, etc.

System Block Diagram

Figure 2:
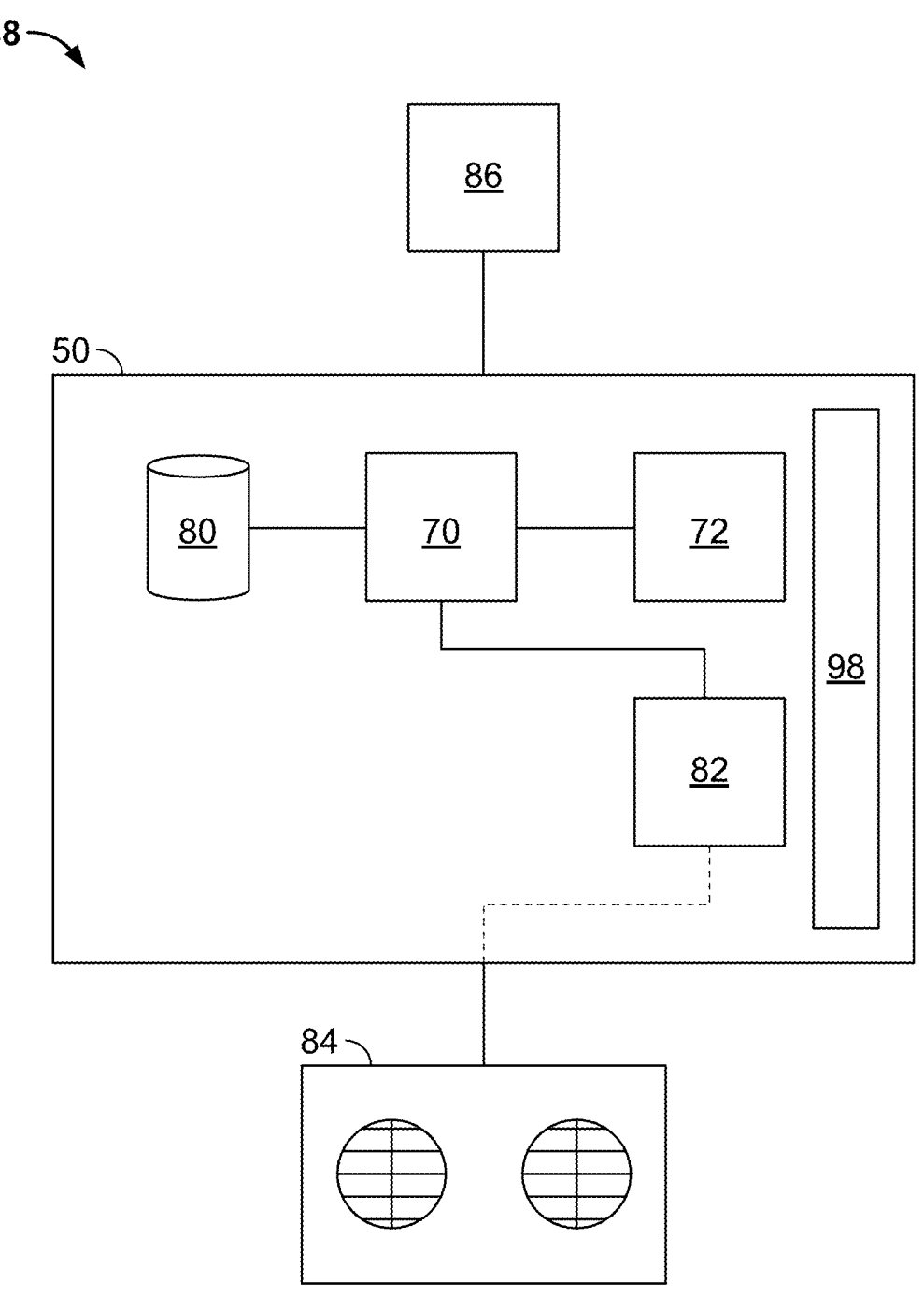
FIG. 2 is a block diagram of a surgical tracking system in accordance with an embodiment of the invention.

FIG. 2 illustrates an intra-procedure image registration system 88 including a workstation or specially programmed computer 50. The workstation 50 shown in FIG. 2 includes at least one processor 70 operable to correct the 3D location of the virtual target as will be described in more detail herein.

Workstation 50 is also shown having a memory device 80 which holds or stores information including imaging, device, marker, and procedural data. The memory device may be a hard drive, for example.

The workstation 50 shown in FIG. 2 is adapted to receive real-time images (e.g., fluoroscopy or endoscopy images) and camera tracking information through various input ports or connectors (e.g., USB port, video port, etc.). A frame grabber card 72 is present to capture individual video frames or images for processing. Real time fluoroscopy images may be obtained by the workstation 50, for example, from continuous fluoroscopy video, video clips, and/or still frames. The workstation is further adapted to send image data to a display using a video card 82. An example of a workstation is a Dell Computer Model No. 7820, Dual Intel Xeon Gold 6136, and a Nvidia Quadro RTX 4000 video card.

The system 88 shown in FIG. 2 also includes a display 84 which may present reports, data, images, results and models in various formats including without limitation graphical, tabular, and pictorial form. In one embodiment of the present invention, a virtual target is superimposed on a live 2D fluoro image of the organ.

It is to be understood, however, that although the system in FIG. 2 is shown with a memory 80 for receiving and storing various information the invention is not so limited. In an alternative embodiment the system may be configured to merely access a memory device such as a USB stick, a CD, or other media storage device.

The system 88 shown in FIG. 2 also includes user input device 86 such as, for example, a keyboard, joystick, or mouse. The user input device allows a user such as the physician to add or input data and information, draw, outline, select, as well as modify planning information and to make notes in the files and records.

In another embodiment the processor 70 is connectable to a memory device through the internet or through another communication line (e.g., Ethernet) to access a network. For example, patient data CT scans may be stored on a server of a hospital and the processor of the instant application is adapted to access such data via a communication module 98 and process the data. Examples of categories of types of communication modules include wireless (e.g., Bluetooth, Wi-Fi) as well as landline and Ethernet.

The displays 84 may be incorporated with the processor in an integrated system (e.g., a laptop, or larger pad-type computer) or the displays may cooperate with the processor from a remote location. A processor may be adapted to send or deliver data across a network to one or more displays, tablet computers, or portable computer devices or smart phones such as the iPhone® manufactured by Apple, Inc. Cupertino, CA, United States. Indeed, although the computer system 88 shown in FIG. 2 includes a number of various components incorporated into a system, the invention is not so limited. The invention is intended to be limited only as defined in the appended claims.

Initial Registration Overview

Figure 3:
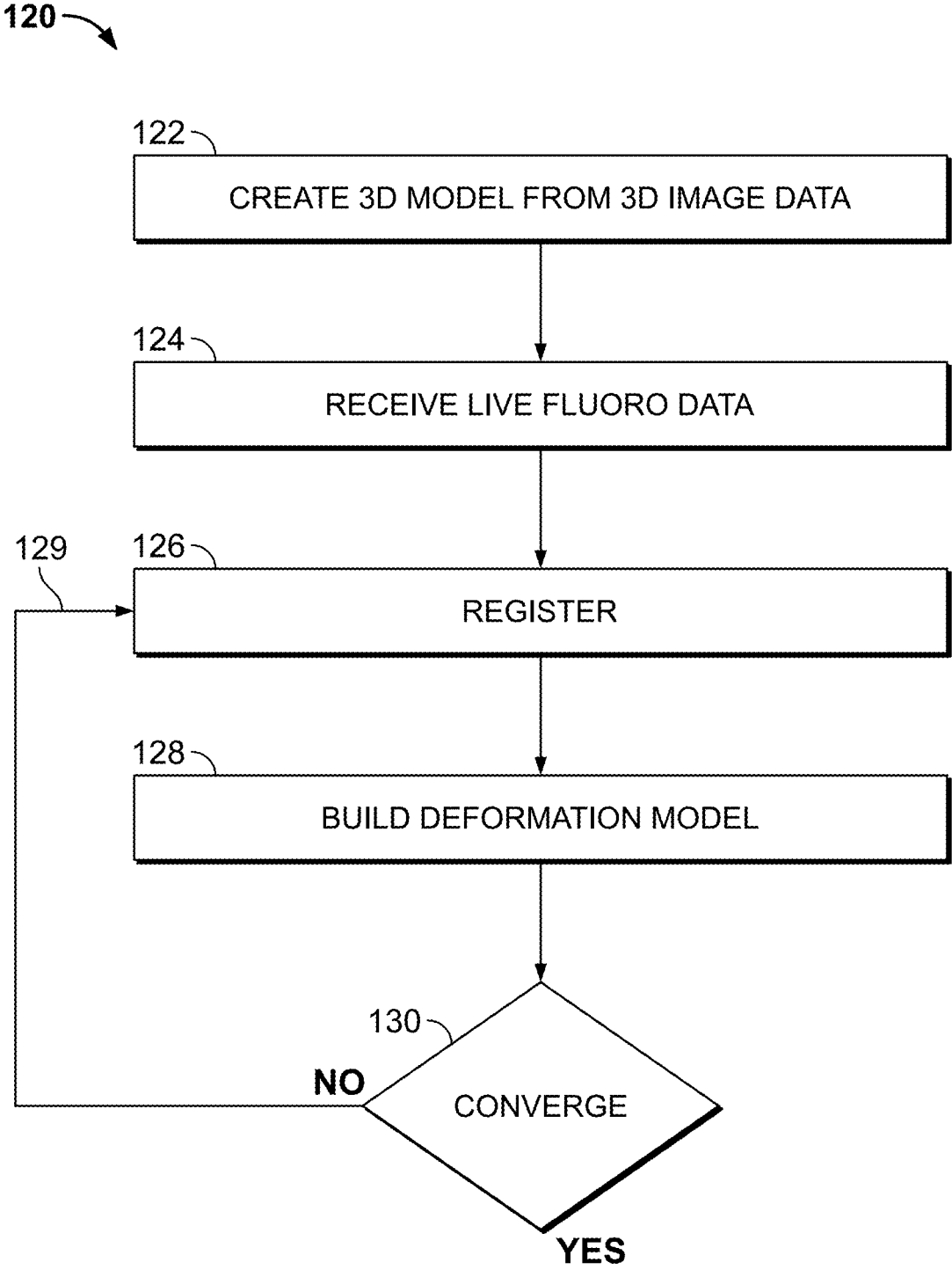
FIG. 3 is a flow chart of a method for registering live 2D fluoro image and camera tracking data to pre-acquired 3D image data.

FIG. 3 is flow chart diagram illustrating a registration method 120 in accordance with the present invention for assisting a physician during a live procedure. The steps may be carried out on a computer or system and include: step 122 creating a 3D model of a body organ; step 124 receiving at least one real-time fluoroscopy image of the body organ including camera tracking information corresponding to the image; step 126 registering a 3D point from the model to a 2D fluoroscopy point in at least one fluoroscopy image; and step 128 deforming the 3D model of the body organ to match the real-time organ.

The step 122 creating a 3D model of a body organ, in one embodiment, includes creating a 3D model of a non-rigid body organ such as the lung in a first body position or first patient position. The 3D model of the body organ is created from input including available image data from the subject such as, for example, high resolution computed tomography (HRCT) scans. The 3D model and associated information is defined in this pre-acquired image data (e.g., CT) coordinate space.

It is to be understood that other acceptable data sets include without limitation MRI, PET, 3D angiographic, and X-ray data sets. In embodiments, the workstation receives a 3D image file, 3D image data set, or a set of 2D images of the organ from which a 3D model of the organ may be computed. The workstation may communicate with a DICOM server, for example, to receive such data sets. An exemplary technique to determine a 3D model of the body organ is disclosed in U.S. Pat. No. 7,756,316 entitled "Method and system for automatic lung segmentation". See also, U.S. Pat. Nos. 7,889,905 and 7,756,563; and Patent Publication No. 2008/0183073 all to Higgins et al.

Next, step 124 recites to receive live fluoro image data. Camera tracking information corresponding to the live images is also gathered. This real time image data of the body organ and fluoroscopic camera and patient board location are obtained while the subject is on the operating table which may not be identical to the first position. For example, the patient may be curled, hyper extended, at a different inspiration level, or otherwise in a different body posture on the operating table than during the pre-operative 3D scans. Certain organs, such as the lung can be deformed due to the subject's body posture, patient orientation, inspiration level, and position. Consequently, the 3D model of the subject in the first position may not match that of the subject in the second real-time position.

Step 126 recites registering the 3D-based model image with the real time fluoroscopy image. Exemplary types of 3D-2D registration may be intensity or location-based.

The intensity-based approach is a preferred embodiment for matching projection (virtual fluoroscopic image) for a given real-time fluoroscopic image. The matching criterion can be mutual-information, cross-correlation, etc. It should also be understood that step 126 provides for registering one point or multiple points. In this manner, a pattern or set of points corresponding to a target or marker, for example, may be registered.

Location-based registration requires the user to go to a known location under fluoroscopy and registration is performed based on the known location or anatomical landmark. For example, the device may be moved to the main carina and the 3D model image is matched to the 2D fluoro image at this known location. See also U.S. Pat. Nos. 7,889,905 and 7,756,563 for registration techniques.

Registering step 126 may be additionally based on application of a 3D deformation model (step 128) to the 3D image. The 3D deformation model is desired because the 3D model of the subject in the first position may not match that of the subject in the second real-time position. The 3D deformation model may either be available before hand or is estimated by step 128. The 3D deformation model applied to the 3D image generates a modified set of 3D locations which are then used for registration.

In one embodiment a loop 129 between step 126 and step 128 is continued until a maximum estimated deformation in step 128 is less than a threshold value. This computation is shown in step 130 of FIG. 3. An example of a threshold value ranges from 0.5 and 5 mm and can be set to about 1 mm. Additionally, step 126 and step 128 can be performed separately or together as joint estimation of CT pose relative to the fluoroscopic camera and deformation model.

A 3D deformation model may be refined such that any point in the fluoroscopy image may be matched with a point in the 3D model.

In one embodiment the 3D model of the body organ is deformed, and a 2D projection image from the 3D model is compared to that of the real time 2D fluoroscopy image. A 2D delta or difference between the image created from the 3D model and the real fluoroscopy image is calculated. This 2D difference gives a constraint on the 3D motion of the reference mark by using the fluoroscopic camera pose. More such constraints can be generated from multiple fluoroscopic images to give the 3D motion of the reference mark. This estimated 3D motion can then be propagated to neighboring 3D points using smoothness constraints or optical flow constraints. An example of optical flow constraint applied to deformation model is given by "Fast Deformable Registration on the GPU: A CUDA Implementation of Demons" by Pinar Muyan-Ozcelik, 2008. A warping algorithm for warping a live image with a model image is also disclosed in U.S. Pat. No. 7,889,905 to Higgins et al. See also U.S. Pat. No. 9,886,760 to Liu et al.

In embodiments, a 3D transformation matrix for the organ and target location is computed by mapping each point in the 3D virtual model (and typically in CT coordinate system/ space) to the 2D live or procedure image data (typically in the patient table or procedure coordinate system/space).

Optical Parameters Fluoroscopic Camera Calibration

Although not specifically recited in the method 120, a fluoroscopic-camera calibration step is typically performed for each new C-arm, when a certain time period (e.g., 6 months) has passed from the last C-arm calibration, or when maintenance has been performed on the C-arm. Calibration data may be obtained off-line and be calculated by acquiring multiple fluoroscopic images of radio-opaque markers to determine such data as the focal lengths and the camera center of fluoroscopic camera, and a representation of the deformation pattern wherein a checkerboard pattern appears curved when viewed in the fluoroscope, and variation of these parameters as the fluoroscope is rotated throughout its range of motion. The calibration factors can be specific to each fluoroscope. Examples of calibrating techniques include those described in Long, L., Dongri, S. (2019). Review of Camera Calibration Algorithms. In: Bhatia, S., Tiwari, S., Mishra, K., Trivedi, M. (eds) Advances in Computer Communication and Computational Sciences. Advances in Intelligent Systems and Computing, vol 924, pp 723-732. Springer, Singapore. https://link.springer.com/chapter/10.1007/978-981-13-6861-5_61.

Fluoroscopic Camera Pose-Patient Table Pose-Calibration

Throughout this invention, reference is made to tracking the camera, namely, tracking the location of the camera using a sensor 44. In performing camera tracking, it is desirable to utilize a common coordinate system and in embodiments, to map the camera location to the patient table landmark (LM) coordinate system or any of the available coordinate systems. With reference again to FIG. 1, in embodiments, the fluoroscope camera image coordinate system is calibrated with a patient table landmark (LM) coordinate system by use of a custom patient board 32, external tracking sensor 44, fluoro tool 46, and patient tool 90 affixed to the patient board 32 which is secured to the operating table 20. An example of an external sensor 44 is the Polaris Spectra or Vega tracker, both of which are manufactured by NDI in Waterloo, Ontario, Canada. As described herein the sensor 44 is operable to track in its 3D space (hereinafter sometimes referred to as the "NDI space") the fluoro tool 46 on the fluoro camera.

Figures 4A, 4B:
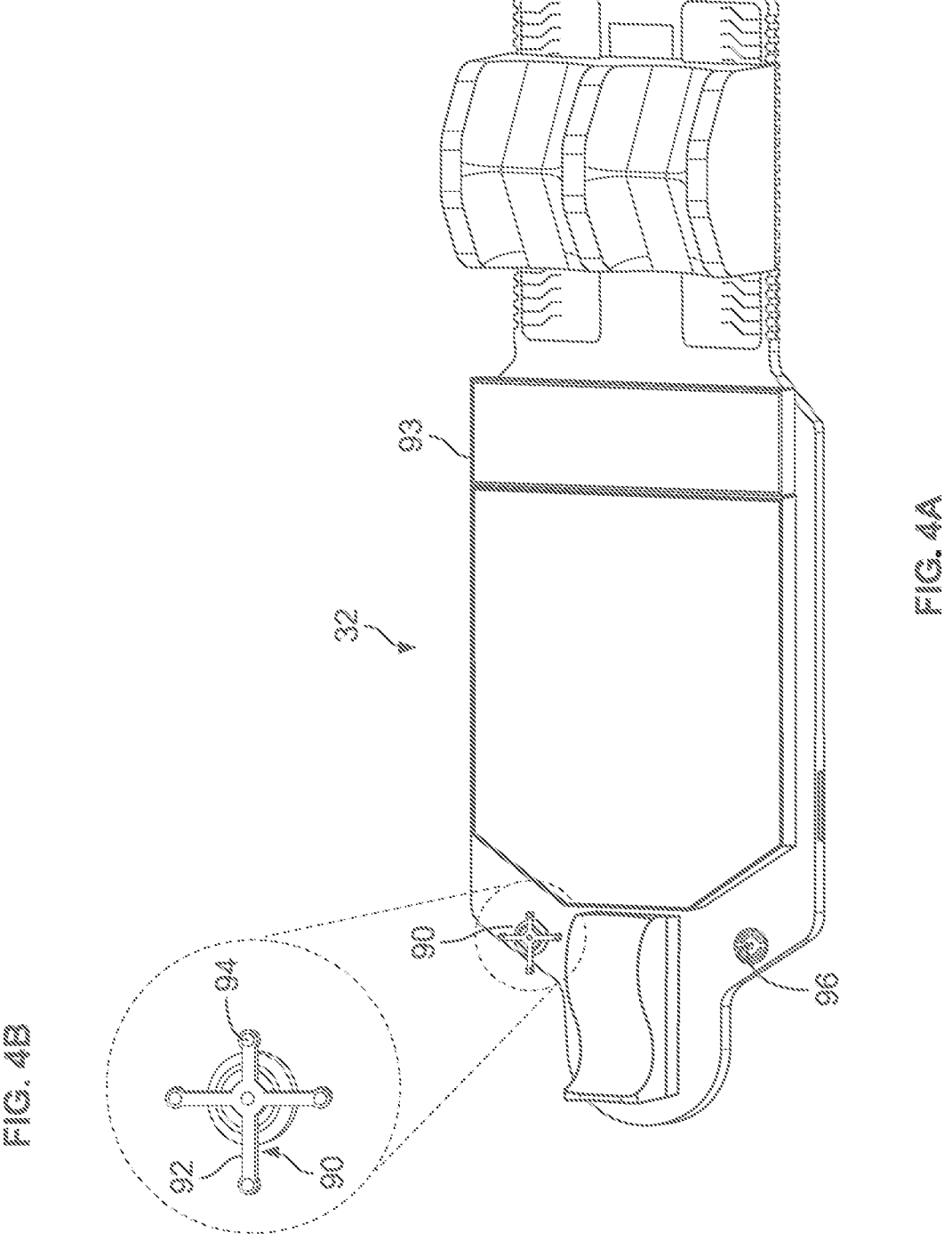
FIG. 4A is a top side perspective view of a patient board including a cross-shaped patient board tool in accordance with embodiments of the invention.
FIG. 4B is an enlarged view of the patient board tool shown in FIG. 4a in accordance with embodiments of the invention.

Additionally, and with reference to FIGS. 4a-4b, the sensor 44 is operable to locate in NDI space the patient tool 90. The patient tool 90 is shown engaged via a mount 96 to the patient board 32. Preferably, patient tool 90 is affixed on the side closest to the workstation 50. The tool 90 is shown having a plurality of arms 92 of different lengths, arranged perpendicular to one another. Markers 94 are shown at the end of each arm. These markers are detectable by sensor 44 to accurately determine location in NDI space.

Figure 4C:
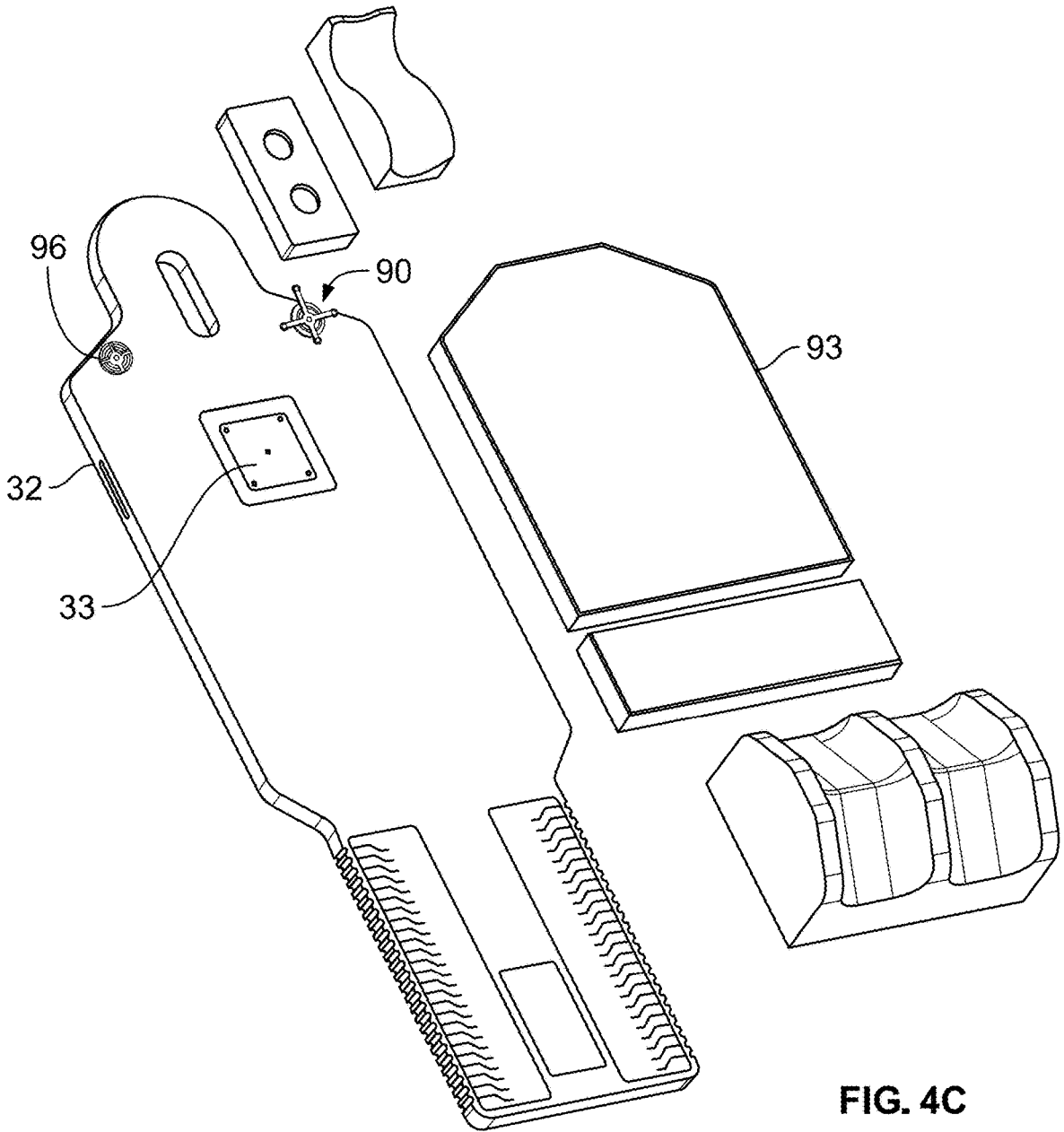
FIG. 4C is an exploded view of the patient board shown in FIG. 4a in accordance with embodiments of the invention.
Figure 4D:
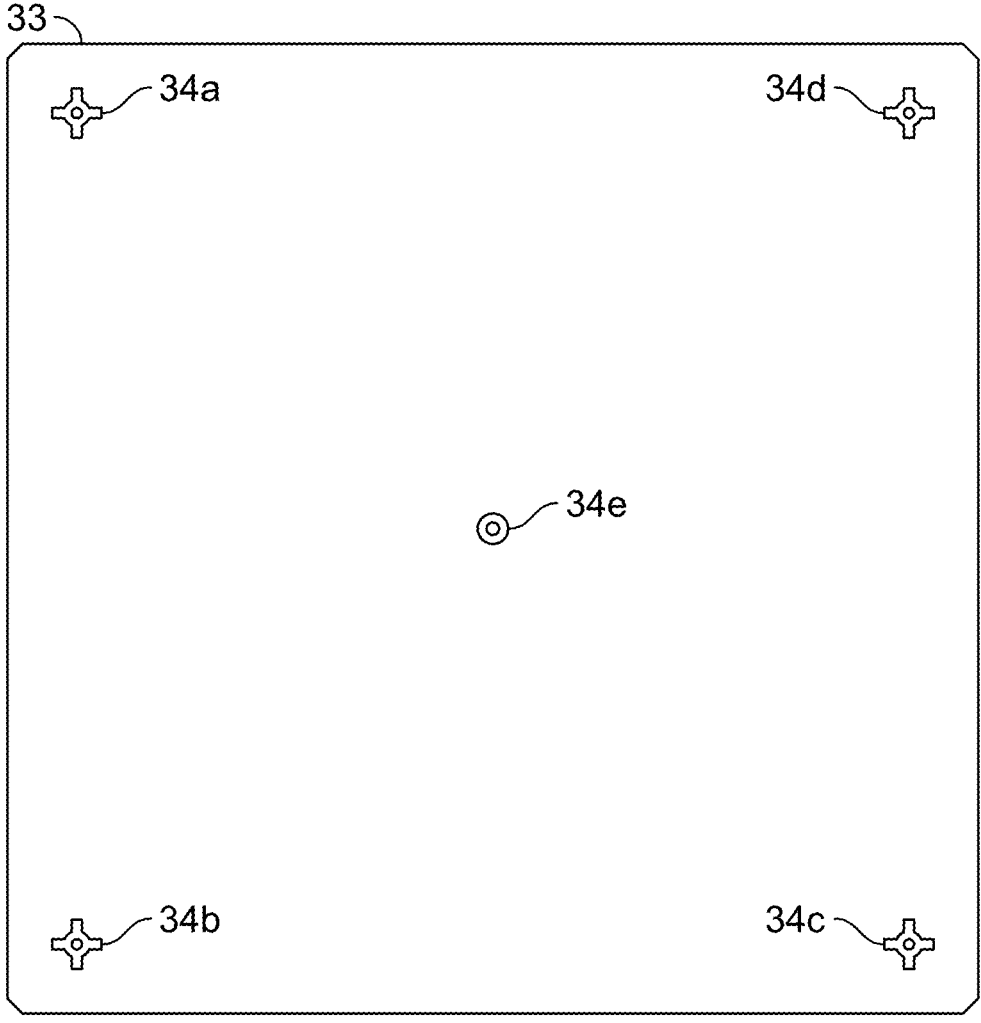
FIG. 4D is an enlarged view of a portion of the patient board shown in FIG. 4c in accordance with embodiments of the invention.

Additionally, with reference to FIGS. 4c-4d, the patient board 32 features a patient landmark (LM) origin plate 33 including a set of radio-opaque markers 34a-34e to define the origin and X-Y axes of the LM coordinate system. The markers 34a-34e are detectable by the fluoroscope camera. The position of the markers 34a-34e relative to the patient tool 90 are fixed and known. Therefore, because the NDI sensor 44 can detect the position of the camera 42 via camera marker 46 and the patient board via the patient tool 90, and the patient table LM origin (also referred to as the live procedural space) is known relative to the patient tool 90, the system can compute the transformation from NDI space to the fluoro Tool 46 space (NDI↔FT) and the NDI space to Patient Tool 90 space (NDI↔PT), and vice versa.

It is also to be understood that although various tools, sensors, specific coordinate transformation or mappings are described above, other optical and coordinate system calibration techniques may be employed with embodiments of the invention. For example, another method for determining the calibration parameters is described in U.S. Pat. No. 9,693,748 to Rai and Wibowo. Examples of a patient table board and a radio-opaque marker are shown in design patent nos. D765865, entitled "PATIENT POSITIONING TABLE", filed Feb. 10, 2015 and D820452, entitled "RADIO-OPAQUE MARKER", filed Jul. 21, 2016, respectively.

Breathing Cycle Compensation

A breathing motion profile corresponding to the respiratory cycle of the patient may also be created from the CT data, or otherwise input to workstation. This may be input or received in the form of, for example, image data of the bronchial tree and airways at multiple points in time corresponding to inhalation, exhalation, and perhaps one or more time points between inspiration and expiration. The data may be processed to identify displacement of tissues and tissue surfaces. A review of the image data across multiple points in time serves to accurately show the breathing motion profile of the patient. An exemplary process for carrying this out is described in "Fast Deformable Registration on the GPU: A CUDA Implementation of Demons" by Pinar Muyan-Ozcelik, 2008 wherein the authors describe using a pair of CT scans acquired from the same patient, one at a full level of inspiration and the second at a full level of expiration. The deformable registration technique described in this paper gives the mapping of each discrete point within the lungs from its geometric location at expiration to inspiration and from inspiration to expiration. From these mappings, the location of any region within the chest can be estimated at points during the breathing cycle. Multiple pairs of scans (e.g., Full inspiration and full expiration scans from more than one person) may also be used to create this data set.

Breathing motion can also be tracked by placing tools to the chest, which are tracked by a sensor. The motion can be used as input and processed within the systems described herein to indicate when a fluoro image should be taken.

Virtual Target Correction

Figure 5:
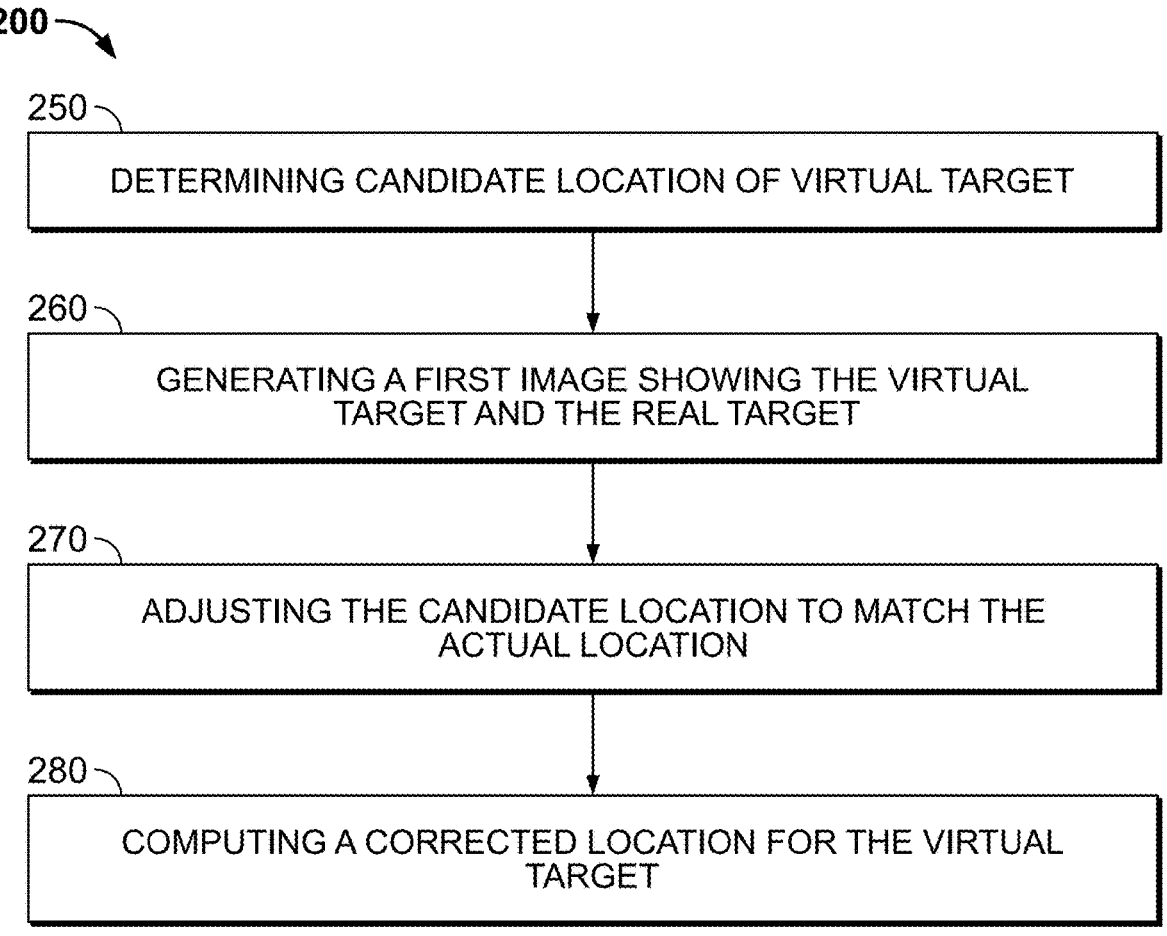
FIG. 5 is a flow chart of a method for virtual target correction in accordance with an embodiment of the invention.

FIG. 5 is flow chart diagram illustrating a virtual target correction method 200 in accordance with embodiments of the invention for assisting a physician during a live procedure.

Step 250 states determining candidate location of the virtual target. This step is performed by mapping the coordinates of the target from the segmented model to the intra-procedural image data set based on the deformation model described above in connection with FIG. 3.

Figure 6:
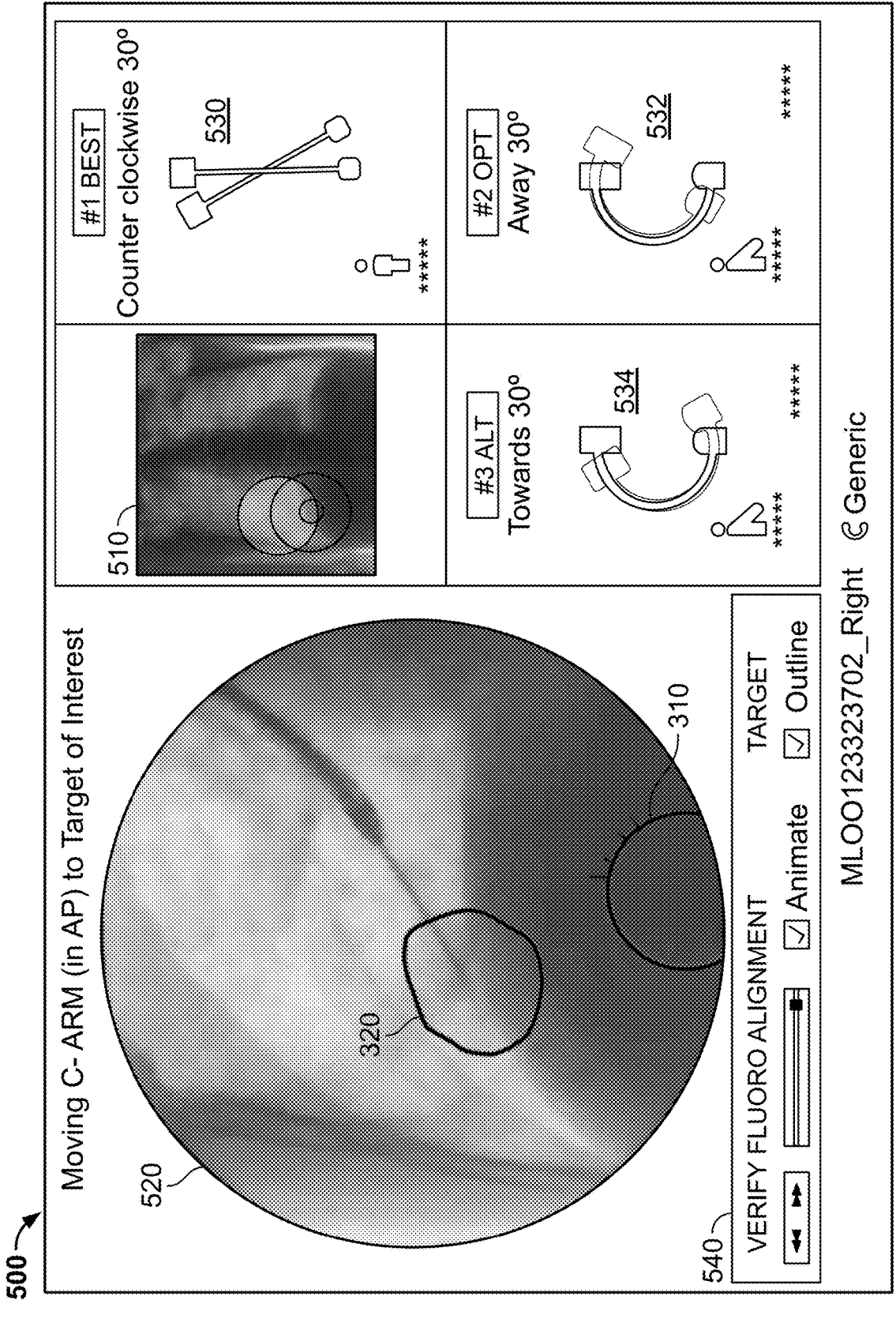
FIG. 6 is a screen shot of a 2D fluoroscope view showing the actual target and virtual target out of alignment.

Step 260 states to generate a first image showing the virtual target and the real target. With reference to FIG. 6, a screen shot of a display is shown including an intra-procedural AP view of a portion of the patient's lung with the virtual target 310 superimposed thereon. The virtual target may be superimposed on the 2D fluoro image based on the known coordinates of the virtual target as determined from step 250 above. However, as shown, the virtual target 310 may not be aligned with the actual target 320. Some of the reasons the virtual target 310 does not align with the actual target 320 include patient positioning and breathing level whether by ventilator or otherwise. Regardless of the cause, misalignment is undesirable because it makes the physician's job more difficult to determine the location of the actual target, and can put the patient at risk.

Figure 7:
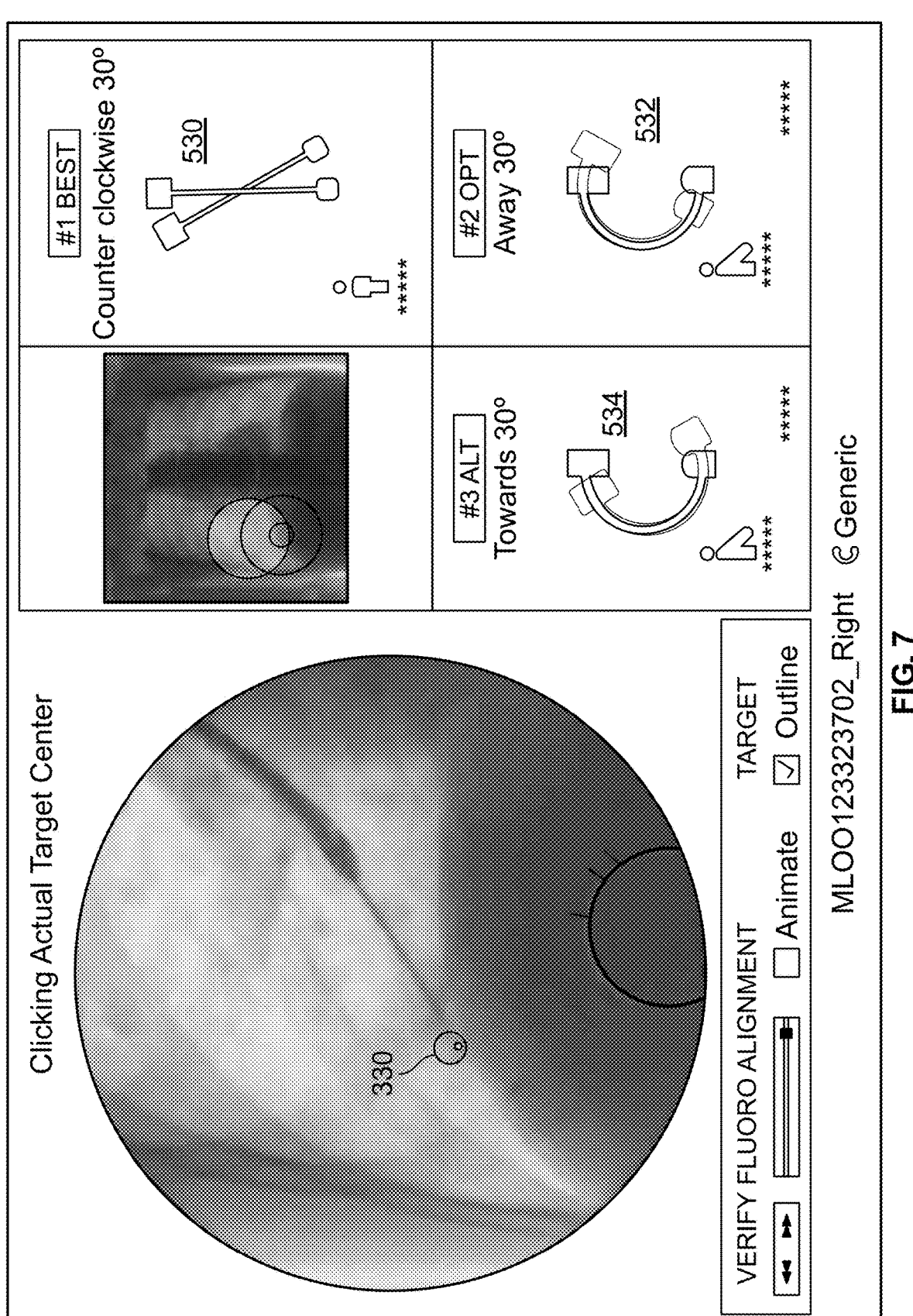
FIG. 7 is a screen shot taken at a first C-arm position and showing the actual target being marked.

Step 270 states to adjust the candidate location to match the real target. With reference to FIG. 7, a fluoroscopy image of the organ and target at a desired breathing level (e.g., the peak inflation) is taken. The view may be AP, or CW, CCW an angle (omega) degree from AP as well as C-Arm away or towards views. Omega may vary. In embodiments, omega ranges from 20-40 degrees from AP. Also, the level of the breathing cycle for the first image is recorded.

The physician then marks the actual target 330 in the first view. In embodiments, the computer is operable to accept user input in the form of highlighting, outlining, dragging (e.g., dragging a shape), or other visual tools using the mouse, keyboard, or touchscreen to select the corrected target location.

In embodiments, the computer is operable to render a virtual marker based on the location of mouse pointer on the screen. The user moves the mouse pointer to the actual target on the screen (preferably the center), and clicks the mouse to record a desired location for the target 330 as shown in FIG. 7.

In embodiments, the system is programmed and operable, upon the click or other signal from the user, to gather and compute the following information to be used for the virtual target correction: 3D location in CT coordinate system, 3D location in fluoro source coordinate system, and the 3D location in patient table landmark (Table LM or procedure space) coordinate system.

Figure 8A:
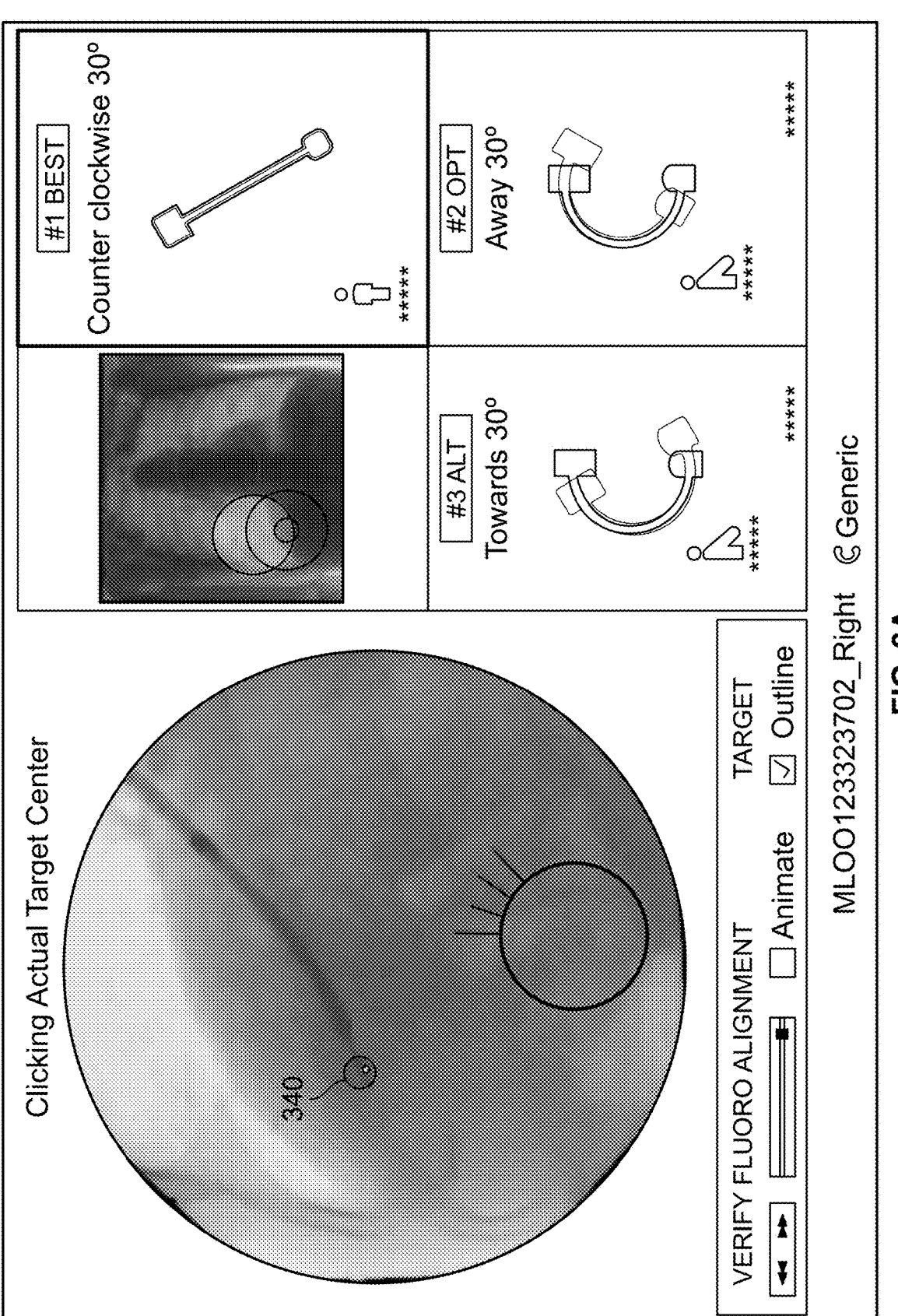
FIG. 8A is a screen shot taken at a second C-arm position and showing the actual target being marked.

In preferred embodiments, and with reference to FIG. 8A, the physician marks the target 340 in a second fluoroscopy view, preferably, at least 30-60 degrees from the first image view angle of the fluoroscope. Optionally, this step may be repeated from a plurality of different scope view angles to provide updated location information for use in correcting the virtual target location discussed below. In embodiments, the computer is programmed to suggest each of the view angles including −30 from AP, +30 from AP, and/or AP, or other angles if the C-arm was calibrated at other angles (e.g., +/−25 degrees from AP).

The second and additional images are preferably taken at the same or similar breathing level as the breathing level recorded for the first image. For each additional image taken, a corresponding set of data is gathered and computed as described above in connection with the first C-arm position image data.

Figure 8B:
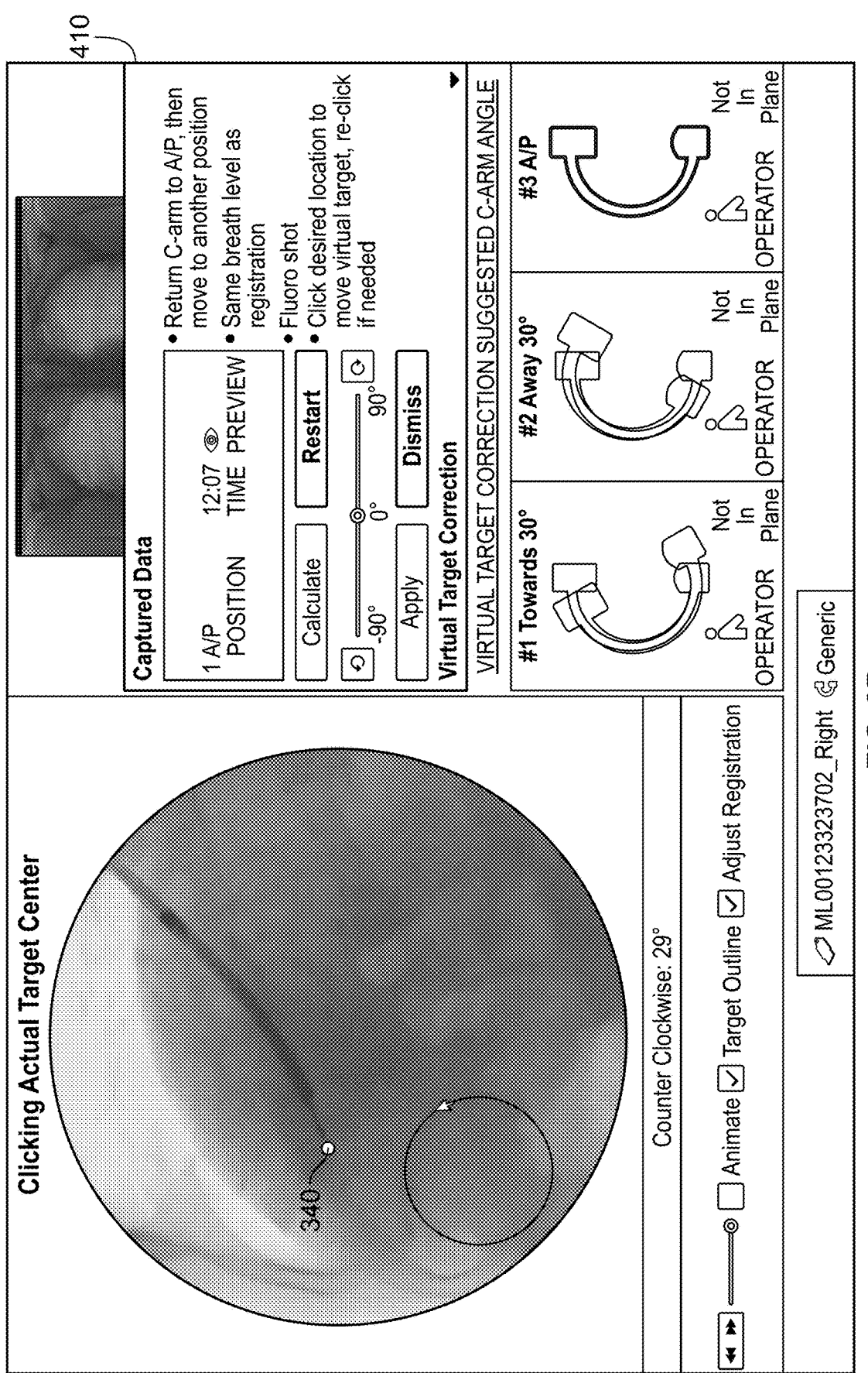
FIG. 8B is another screen shot at a selected C-arm position and showing a VTC panel window.

FIG. 8B is another screen shot showing the target 340 being marked in a second view (Counter Clockwise 29 degrees). FIG. 8B also includes a VTC panel window 410 which opens when the adjust registration tab is selected. The VTC panel window 410 provides a user interface in accordance with embodiments of the invention for the physician to conveniently compute the corrected location for the virtual target as described herein.

Step 280 states computing the corrected location for the virtual target.

11

Figure 9:
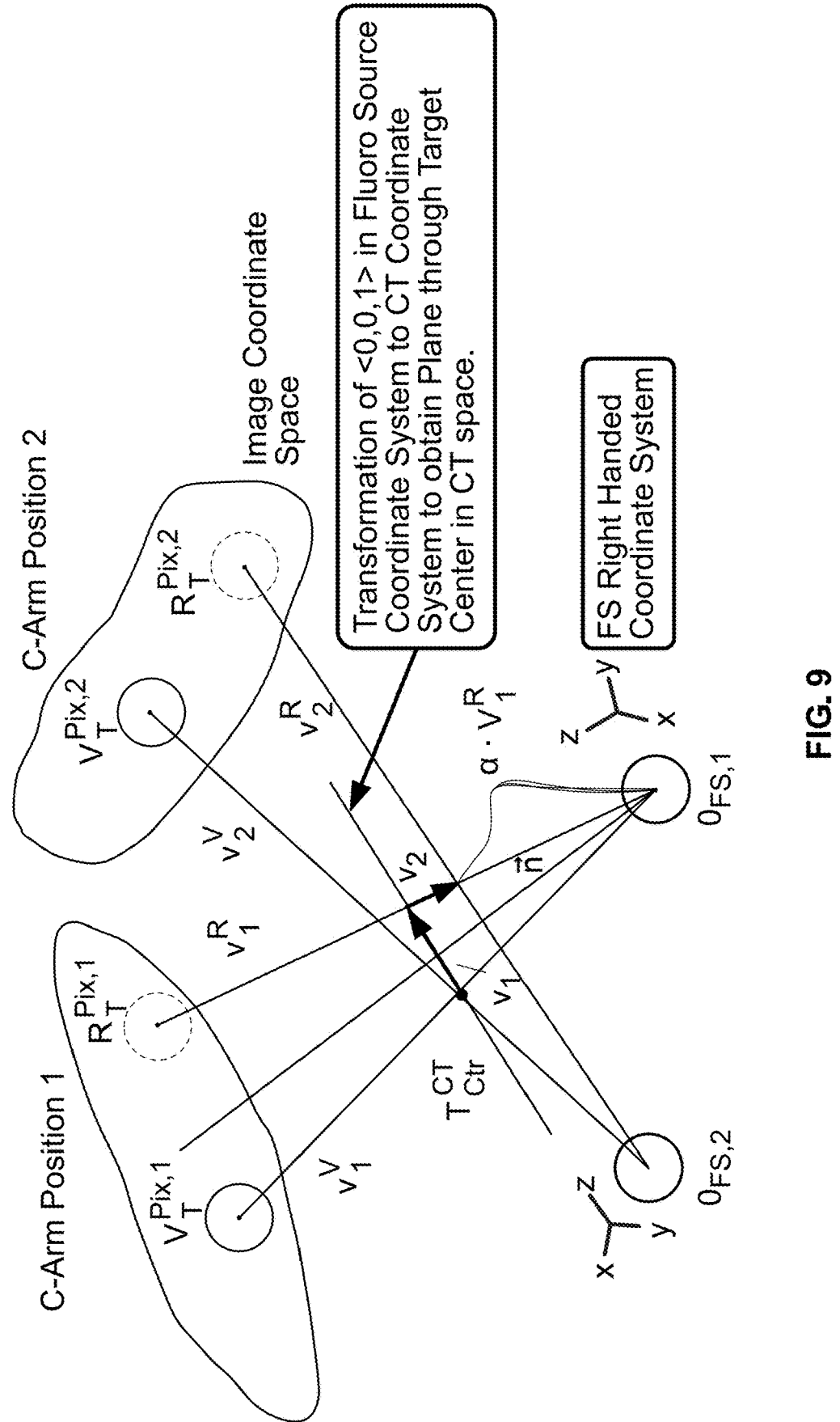
FIG. 9 is a schematic diagram showing the real and virtual target in CT coordinate system space and fluoro coordinate system space at two different C-arm positions.

With reference to FIG. 9, we desire to update the CT-Table LM transformation matrix so that the initial virtual target location $$\left(T_{Ctr}^{CT}\right)$$

is accurately mapped to the real target location in the fluoro image coordinate system/space.

To this end, we need to compute vectors $v_1$ and $v_2$ where:

$$v_1^V + v_1 = v_1^R \Rightarrow v_1 = v_1^R - v_1^V$$

We then compute $v_1$ based on the above gathered information where $$v_1^V$$

represents the vector from the fluoro source origin at C-arm position 1 to target center in CT space. To convert points in fluoro source coordinate system at C-arm position 1 to points in CT space, we need to compute the transformation $M_{FS,1 \to CT}$. The transformation $M_{FS,1 \to CT}$ is obtained via the following transformations: 1) Fluoro source to fluoro tool at C-arm position 1 transformation is obtained through C-arm calibration and is denoted by FS→FT. 2) Fluoro tool to NDI tracker transformation is obtained through tracking of the fluoro tool by the NDI tracker as is denoted as FT→NDI. Similarly, the transformation from NDI tracker to patient tool is obtained by the NDI tracker and is denoted by NDI→PT. 3) Patient tool to patient table landmark coordinate system transformation is obtained through patient table calibration and is denoted by PT→PTL. 4) Patient table landmark to CT transformation is obtained from registration computation and is denoted by PTL→CT. From the above transformation, we obtain the transformation $M_{FS,1 \to CT}$ through FS→FT→NDI→PT→PTL→CT. Step 4 is performed as described above in connection with FIGS. 4A-4D; and Then, $$v_1^R$$

is computed by 1) obtaining the user clicked point on screen where real target center is. The user clicked point is represented in screen space coordinate system. 2) Converting the screen space coordinate system point to image coordinate system space, where image coordinates are represented in pixel units. 3) Based on the calibration of the C-arm at Position 1, a ray is associated to the image coordinates in Step 2. This ray is defined in fluoro source coordinate system and must be transformed in CT space by $M_{FS,1 \to CT}$. The resulting ray will be defined as $$\tilde{v}_1^R.$$

4) Scaling the transformed ray in Step 3 allows us to intersect a plane defined by the normal to the fluoro source containing the CT target center. The vector $v_1$ will lie in the plane defined by the normal to the fluoro source and emanates from the CT target center to the scaled ray defined in Step 3 (which intersects with the plane formed from the normal of the fluoro source). The equation defining the plane is $\langle \vec{n}, \vec{x} - p \rangle = 0$ where $\vec{n}$ is computed by using the rotational component of $M_{FS,1 \to CT}$ applied to the vector $\langle 0,0,1 \rangle$ and the point p can be computed using the projection of $$v_1^V$$

onto $\vec{n}$. The scaling factor $$\alpha = \frac{\langle \vec{n}, p \rangle}{\langle \vec{n}, \tilde{v}_1^R \rangle}$$

applied to $$\tilde{v}_1^R$$

yields $$v_1^R.$$

Next, we compute $v_2$ where $v_2$ may be obtained by: Initially determining the shortest distance between $$v_1^R$$

and $$v_2^R$$

where $$v_1^R$$

was determined above and $$v_2^R$$

can be obtained similarly as described above in connection with determining $$v_1^R$$

except for at C-arm position no. 2 or $(0_{FS,2})$.

13

If $$v_1^R$$

and $$v_2^R$$

intersect, the point of intersection is located and the vector $v_2$ is computed.

If $$v_1^R$$

and $$v_2^R$$

do not intersect, then they are skew lines in 3D space, and we can apply least squares fitting method to find the points where both lines are the closest.

In embodiments, a bisection type method is used to match the clicked point with the C-Arm position 2.

After translation has been computed as shown above, the projection of the virtual target will be on the actual target. However, we also need to correct the rotational aspect of the virtual fluoro and procedure fluoro. In embodiments, correction of the rotational aspect is performed by incrementally rotating the rotation component of the CT→Table LM transform (e.g., by user manual adjustment) to visually align a common feature, preferably a rigid feature such as spine. In embodiments, the user visually aligns the spines in the virtual fluoro and real fluoro, i.e., parallel spines between virtual fluoro and real fluoro.

The rotation is done about the target center (keeping target fixed) in the plane parallel to the patient board. The current fluoro shot can be used in this process.

After we have the translation and rotational aspects to map the virtual target center to the procedural fluoro target center, and $v_1$ and $v_2$ are obtained as described above, we can update the registration transform matrix (CT coordinate system to Table Landmark coordinate system transformation, namely CT→Table LM).

Figure 10:
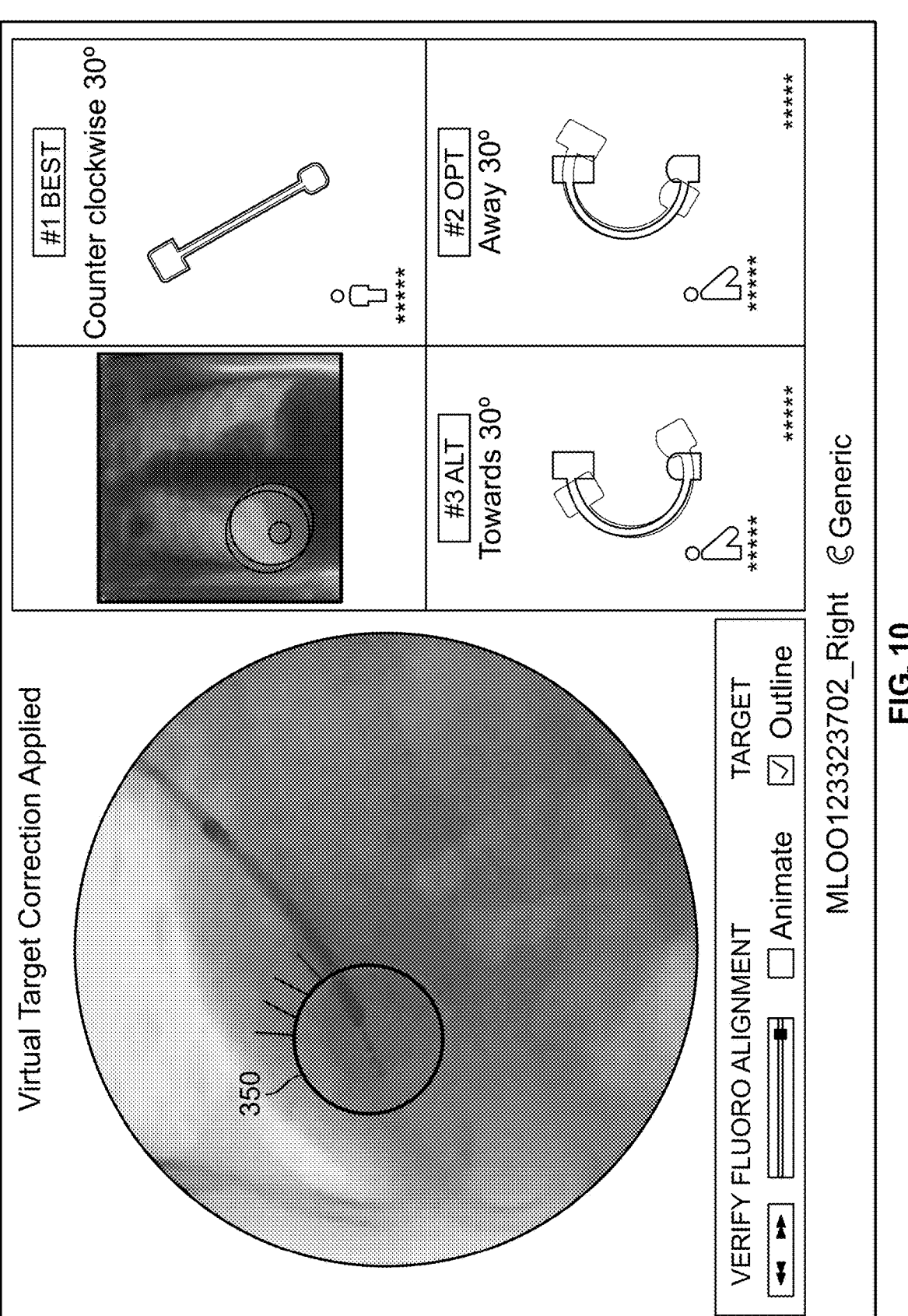
FIG. 10 is a screen shot at the first C-Arm position showing the corrected virtual target in alignment with the actual target.
Figure 11:
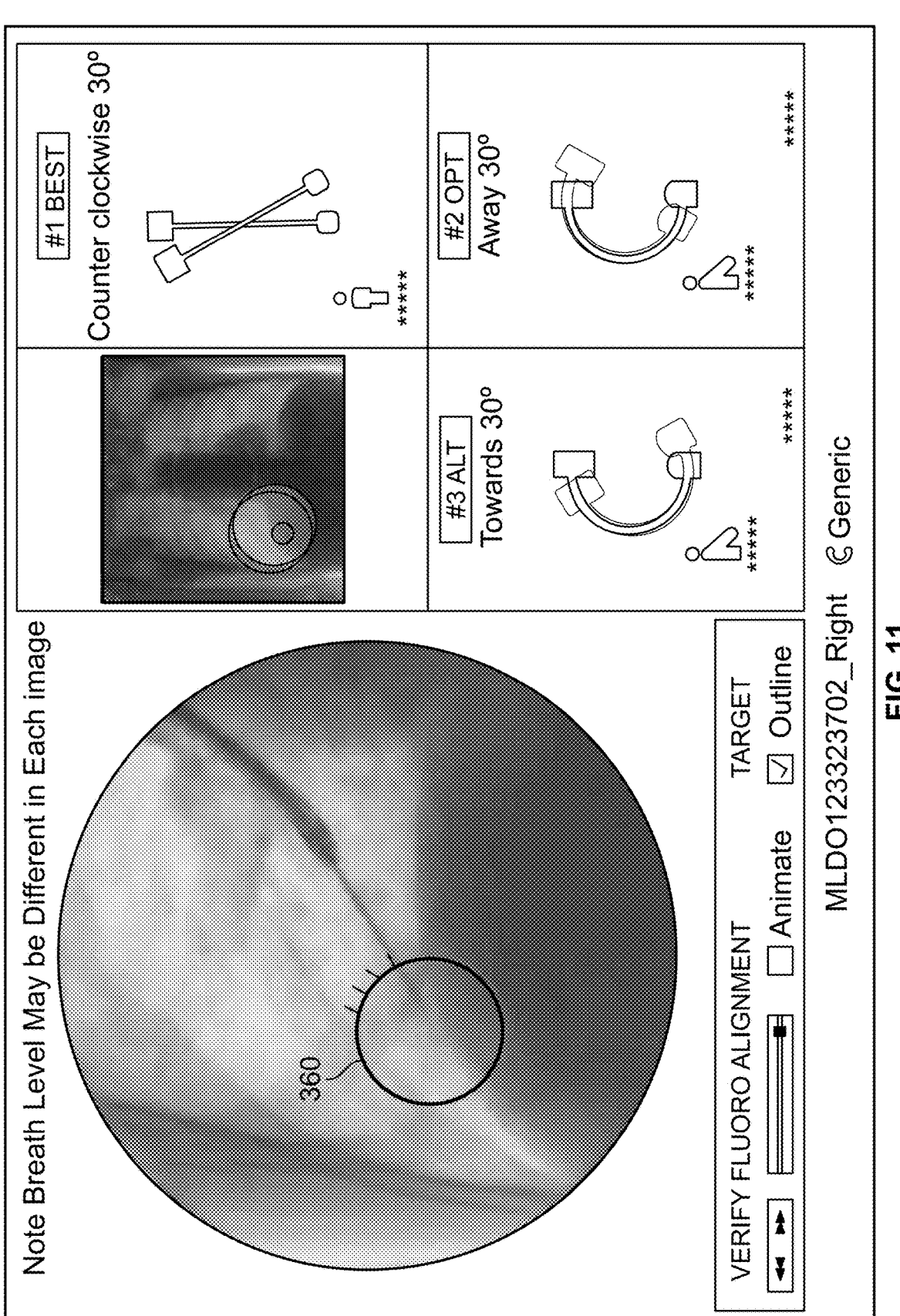
FIG. 11 is a screen shot at the second C-Arm position showing the corrected virtual target in alignment with the actual target.

In embodiments, the method can further include displaying the corrected virtual target. With reference to FIGS. 10-11, the corrected virtual target 350, 360 is shown at two different C-arm positions, namely, CCW 30 and AP, respectively. Amongst other benefits, displaying provides tracking and guidance information to the physician. In one embodiment, a virtual target is superimposed onto a 3D view of the body organ. Additionally, because the 3D location of the virtual target is computed as described above, it may be superimposed on the model projection 2D fluoroscopy view. Indeed, a number of views showing the target, as well as any surgical devices, additional markers, routes, indicia and planning information may be displayed with model or real images of the organ.

Graphical User Interface

With reference again to FIG. 6, various windows of a graphical user interface (GUI) 500 in accordance with an embodiment of the invention are shown. GUI 500 is shown including a static fluoro window 510, fused fluoro window 520, suggested angles windows 530, 532, 534 and options window 540.

Figure 12:
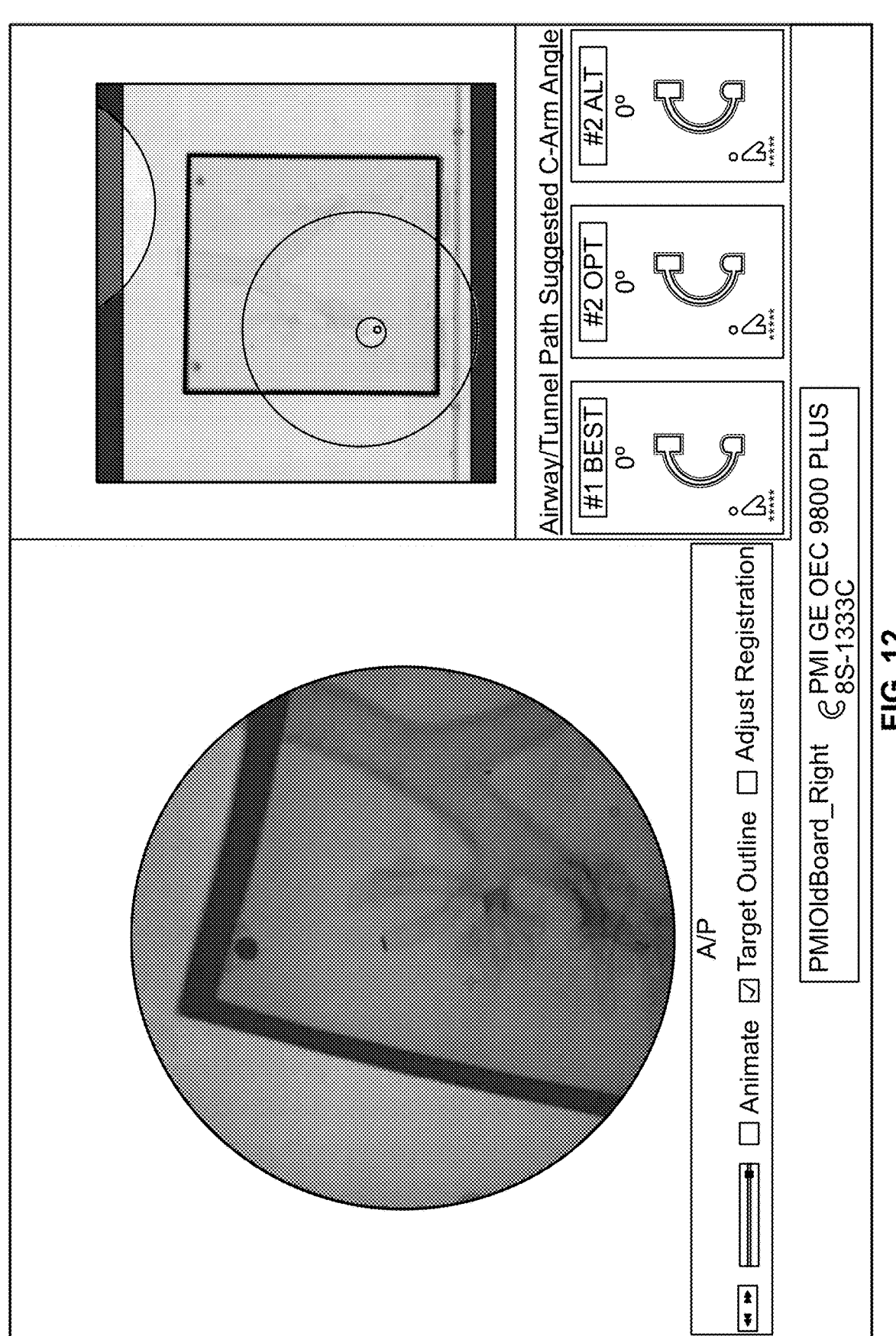
FIG. 12 is an anterior posterior (A/P) view of a phantom model of an airway of the patient.

Static fluoro window 510 is configured to show a full patient fluoro image based on the CT image data for a user selected C-arm position. Alternatively, as shown in FIG. 12, an A/P static fluoro view may be shown in place or in addition to the static fluoro window shown in FIG. 6.

With reference again to FIG. 6, Fused fluoro window 520 is configured to show the live 2D fluoro image with the virtual target 310 computed from the pre-acquired CT image data and output from registration as described above on the 2D fluoro image. As described above, the computed virtual target 310 may not align with the actual target 320.

Windows 530, 532, and 534 show suggested angles for the C-arm. Categories of suggested angles to select include (a) suggested C-arm angles 532 for best view of visible target when using the VTC discussed herein, and (b) suggested C-arm 534 for best tunnel path to target.

In embodiments, the C-arm angles are provided in order of the $1^{st}$ best, $2^{nd}$ best, and $3^{rd}$ best for a view of the tunnel to target from the airway wall.

In embodiments, VTC suggested angles are based on the contrast difference between the virtual target and the surroundings. In embodiments, the C-arm angle providing the highest contrasting difference is the first suggested angle 530, the C-arm angle providing the second highest contrasting difference is the second suggested angle 532, the C-arm angle providing the third highest contrasting difference is the third suggested angle 534, and so forth.

Window 540 shows various user options. Options include animate, target outline, and registration adjust/virtual target correction (VTC).

Selecting the animate tab provides an animation between the current C-arm position fluoro image and the corresponding virtual fluoro. During the VTC workflow, this information can be used to orient live and virtual anatomy such as, e.g., the spine and ribs.

Selecting the outline tab provides the user tools to mark or identify the real target in the image. Examples of tools include tracing, pointing/clicking, and dragging. In embodiments, when the outline tab is selected, the virtual target 310 shown in the fused fluoro may be dragged by the user to the real target.

Figure 13A:
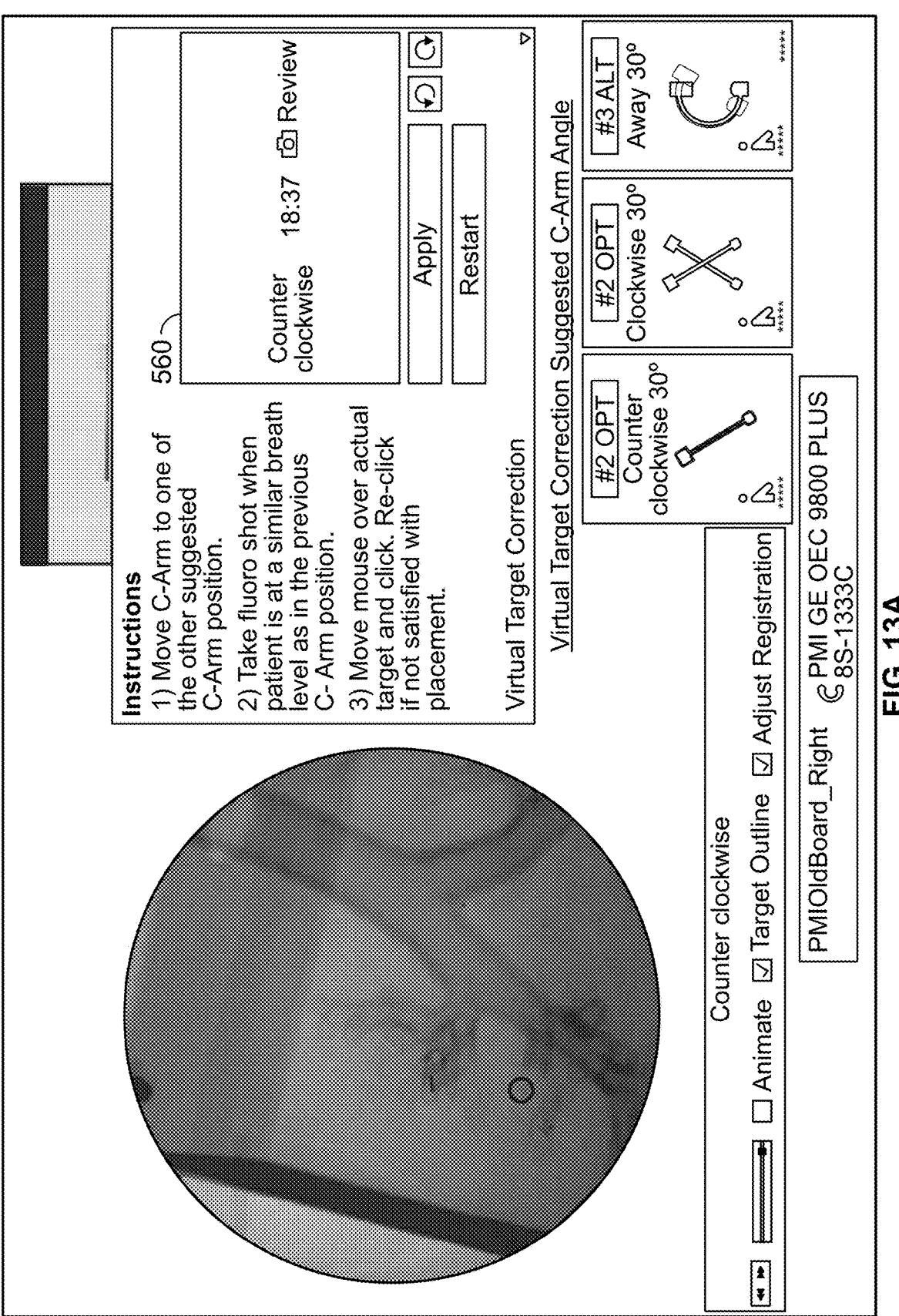
FIGS. 13A-13B are screen shots of various graphical user interfaces in accordance with embodiments of the invention.

With reference to FIG. 13A, an "adjust registration" tab is presented in accordance with embodiments of the invention. When the adjust registration tab is selected, VTC panel window 560 is opened. VTC panel window 560 is shown including a window for instructions, virtual target incremental adjustment controls with undo feature, capture ("apply") of selected registration dataset (corresponding to $1^{st}$ shot, $2^{nd}$ shot, etc.), recalculate, and reset (namely, restart) tab. VTC options window also includes an option to return to original registration and exit tab.

Figure 13B:
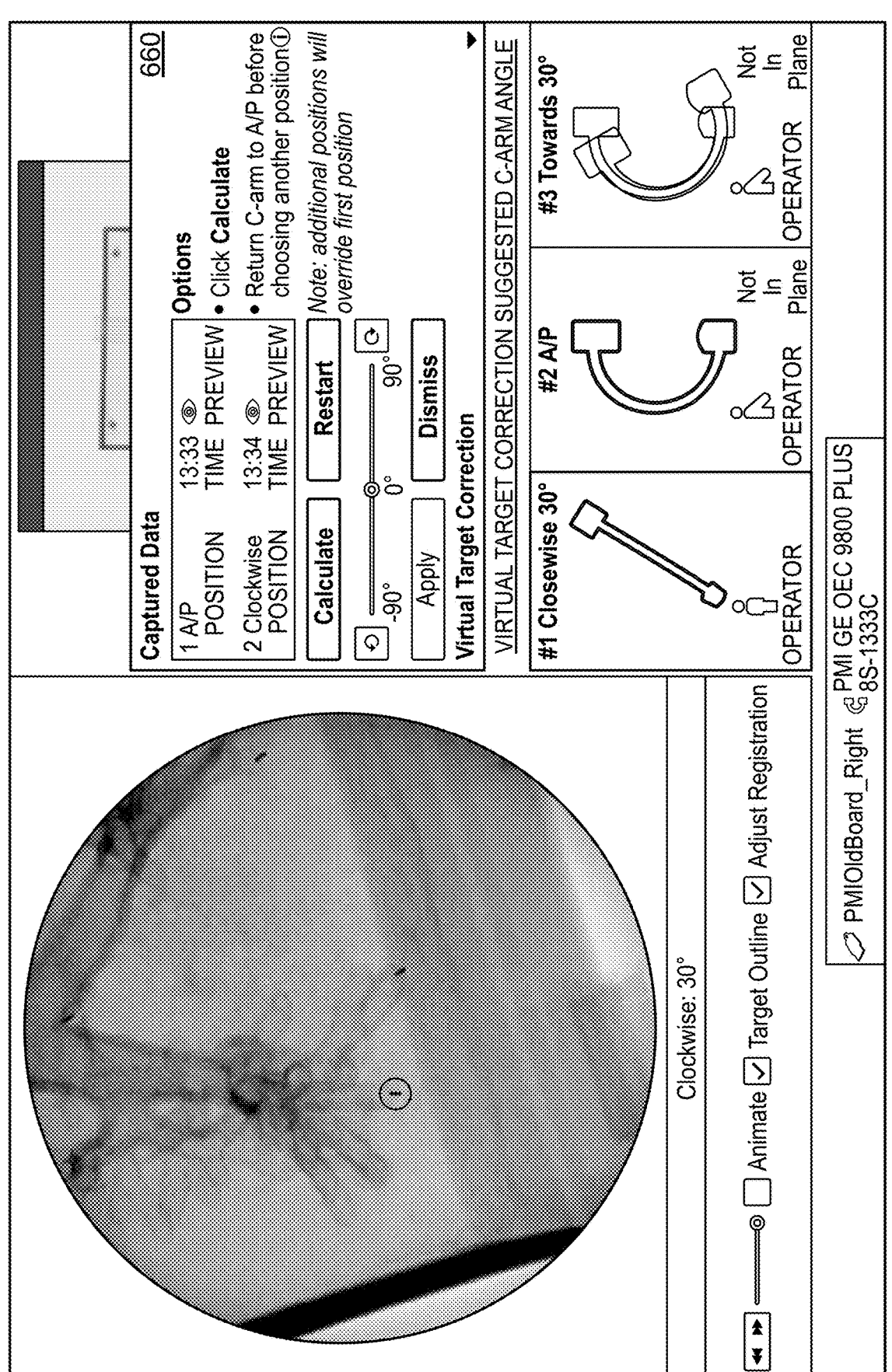

FIG. 13B shows another VTC panel window 660 in accordance with embodiments of the invention which opens when the adjust registration tab is selected. VTC panel window 660 is shown including a window for "Options" which lists user instructions, a "Calculate" tab which commences computation of the virtual target correction, an "Apply" tab which applies the selected registration dataset (corresponding to $1^{st}$ shot, $2^{nd}$ shot, etc.), a "Restart" tab which recalculates the virtual target computation, and "Dismiss" tab which cancels the instant or current VTC, and returns to the original registration.

Additional windows and tabs with corresponding functionality may be added to carry out the objects and features described herein. Additionally, other modifications and variations can be made to the disclosed embodiments without departing from the subject invention.

We claim:

1. A method for correcting location of a virtual target in a patient during a live procedure comprising:

receiving a pre-procedure image data set of the patient including an organ and a real target;

segmenting the organ and the real target from the pre-procedure image data set;

receiving a live procedure image data set of the patient including the organ and the real target at an actual location and camera tracking information;

registering the pre-procedure image data set and the live procedure image data set to determine an initial pre-procedure to live procedure transformation matrix;

determining a candidate location of a virtual target for the real target based on the pre-procedure to live procedure transformation matrix;

generating a first image at a first view angle showing the virtual target and the real target;

adjusting the candidate location of the virtual target to match the actual location of the real target in the first image; and computing a corrected location for the virtual target based on the adjusting step, including forming a calibrated 3D ray, based on the camera tracking information, in a fluoroscope source coordinate system corresponding to the adjusted location in the first image and mapping the 3D ray into the pre-procedure coordinate system using the transformation matrix.

2. The method of claim 1, comprising:

generating a second image at a second view angle showing the virtual target and the real target;

adjusting the candidate location of the virtual target to match the actual location of the real target in the second image; and wherein computing the corrected location for the virtual target is based on the adjusting step performed on the first image and the adjusting step performed on the second image.

3. The method of claim 2, wherein the first view angle is at least 20 degrees from the second view angle, and optionally, wherein the first view angle is at least 20 degrees from anteroposterior (AP) in a first direction, and the second view angle is at least 20 degrees from AP in a second direction opposite to the first direction.

4. The method of claim 1, wherein adjusting the candidate location of the virtual target to match the actual location of the real target is performed by dragging the virtual target to the actual target in the first and second image.

5. The method of claim 1, wherein adjusting the candidate location of the virtual target to match the actual location of the real target is performed by marking a feature in the actual target or in the vicinity of the actual target in the first and/or second image.

6. The method of claim 5, wherein the feature is the center or, optionally, the perimeter of the actual target.

7. The method of claim 2, wherein the second image is taken at the same patient breath level as the first image and, optionally, the user is prompted when to take second image based on breathing phase tracking and the point in the breathing phase that the first image was taken.

8. The method of claim 2, wherein the computing step comprises determining a translation aspect for the corrected location.

9. The method of claim 8, further comprising computing a rotational aspect for the corrected location.

10. The method of claim 9, wherein the rotational aspect is based on incrementally rotating the procedure image relative to the live image and about the target center until a feature present in both images is aligned.

11. The method of claim 10, comprising updating the initial transformation matrix based on the translation and rotational aspects.

12. A system for correcting a location of a virtual target comprising a processor programmed and operable to:

segment an organ and a real target from a pre-procedure image data set;

receive a live image data set of a patient including the organ and the real target and camera tracking information;

register the pre-procedure image data set and the live image data set according to an initial 2D-3D transformation matrix;

generate a first image at a first view angle showing the real target at an actual location and the virtual target at a candidate location superimposed thereon based on the initial 2D-3D transformation matrix; and compute a corrected location for the virtual target based on user adjustment to the candidate location of the virtual target in the first image, including forming a calibrated 3D ray, based on the camera tracking information, in a fluoroscope source coordinate system corresponding to the user adjustment, and mapping the 3D ray into a pre-procedure coordinate system using the initial 2D-3D transformation matrix.

13. The system of claim 12, wherein the processor is further operable to:

generate a second image at a second view angle showing the real target and the virtual target; and compute the corrected location for the virtual target based on the user adjustment to the candidate location performed on the first image and user adjustment to the candidate location performed on the second image.

14. The system of claim 13, wherein each of the first image and second image is a 2D image.

15. The system of claim 14, wherein the corrected location for the virtual target is a 3D location.

16. The system of claim 15, wherein the processor is further operable to update the initial 2D-3D transformation matrix subsequent to the computing the corrected 3D location for the virtual target.

17. The system of claim 12, wherein the user adjustment comprises a feature marked by the user in the actual target or in the vicinity of the actual target in the first and/or second image.

18. The system of claim 12, wherein the processor is programmed and operable to compute a translation aspect for the corrected location.

19. The system of claim 18, wherein determining the translation aspect from the candidate location to the actual location is based on determining vectors $v_1$ and $v_2$ in the initial pre-procedure coordinate space, where:

(a) vector $v_1$ is based on the virtual target vector $$\left( v_1^r \right)$$

for the candidate virtual location and the real target vector $$\left(v_1^R\right)$$

for the actual location at the first view angle, and
(b) vector $v_2$ is based on the vector $v_1$ and the real target vector $$\left(v_2^R\right)$$

for the actual location at the second view angle.

20. The system of claim 19, wherein $$v_1^V$$

is based on:

sensing, in sensor space, a first position of a fluoro tool associated with the camera;
 calibrating the first position of the fluoro tool to the fluoro source coordinate system;
 sensing, in sensor space, the location of a patient tool affixed to a patient table supporting the patient;
 calibrating the location of the patient table to the fluoro source coordinate system; and
 the initial pre-procedure to live procedure transformation matrix.

21. The system of claim 20, wherein $v_2$ is based on determining the shortest distance between $$v_1^R$$

and $$v_2^R.$$

22. The system of claim 21, and wherein $$v_2^R$$

is obtained similarly as described above in connection with determining $$v_1^R$$

except for at C-arm position no. 2; and
 If $$v_1^R$$

and $$v_2^R$$

intersect, the point of intersection is located and the vector $v_2$ is computed; and
 If $$v_1^R$$

and $$v_2^R$$

do not intersect, least squares fitting is applied to find the points where both lines are the closest.

23. The system of claim 18, wherein the processor is further programmed and operable to compute a rotational aspect for the corrected location.

\* \* \* \* \*